United States Patent

Sano et al.

[11] Patent Number: 5,181,055
[45] Date of Patent: Jan. 19, 1993

[54] FUNDUS CAMERA

[75] Inventors: Eiichi Sano; Hiroshi Minegishi, both of Tokyo, Japan

[73] Assignee: Kabushiki Kaisha Topcon, Tokyo, Japan

[21] Appl. No.: 741,870

[22] Filed: Aug. 8, 1991

[30] Foreign Application Priority Data

Aug. 9, 1990 [JP] Japan .................. 2-211357

[51] Int. Cl.⁵ .............................................. G03B 29/00
[52] U.S. Cl. ....................................... 354/62; 351/206
[58] Field of Search ................. 354/62; 351/206–208, 351/213, 221

[56] References Cited

U.S. PATENT DOCUMENTS 4,690,525 9/1987 Kobayashi et al. ................ 351/206

Primary Examiner—Michael L. Gellner
Assistant Examiner—David M. Gray
Attorney, Agent, or Firm—Finnegan, Henderson, Farabow, Garrett and Dunner

[57] ABSTRACT

This invention discloses a fundus camera which can take fluorescent photographs by infra-red light and other types of photographs.

It comprises detecting means for detecting whether or not the photograph being taken is a fluorescent photograph by infra-red light, means for automatically setting the amount of light emitted by a photographic source when the photograph being taken is not a fluorescent photograph by infra-red light, and changing over to manual setting of the amount of light emitted by said photographic source when the photograph being taken is a fluorescent photograph by infra-red light, according to information provided by said detecting means.

7 Claims, 1 Drawing Sheet

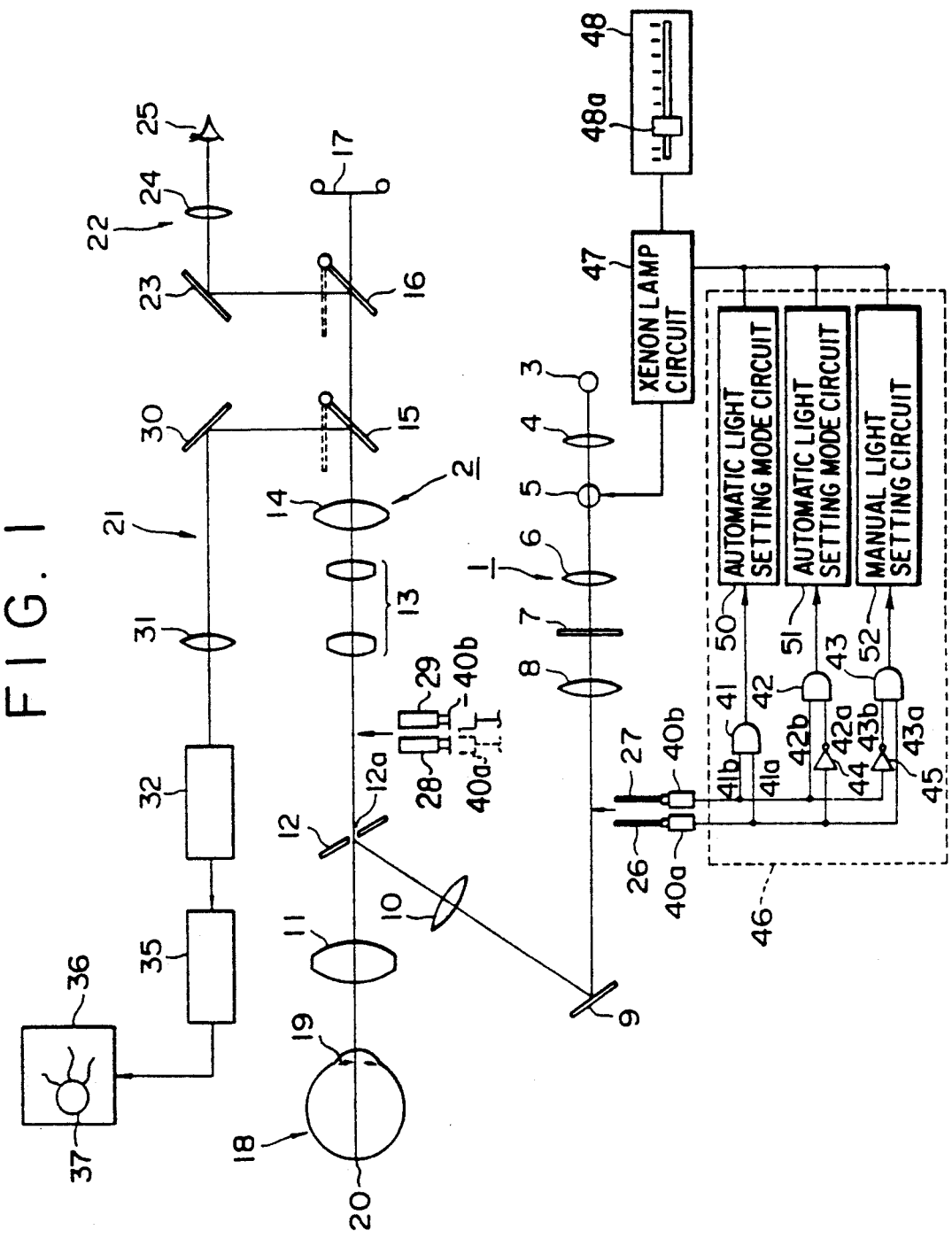

FUNDUS CAMERA

BACKGROUND OF THE INVENTION

1. Field of the Invention

This invention relates to an improvement of a fundus camera which takes fluorescent photographs by infra-red light and by light other than infra-red light.

2. Description of the Prior Art

Conventionally, a fundus camera is known in the prior art which is capable of taking color photographs or black and white photographs of the fundus of a subject's eye by illuminating it with visible light, and which is also capable of taking fluorescent photographs of the fundus by illuminating it with visible light thereby exciting a fluorescent agent to fluoresce.

In this type of fundus camera, the amount of light from the photographic light source was automatically set depending on the photographic mode employed. Further, provision was also made for changing the amount of light emitted by the source by means of a manual switch.

However, fundus cameras are now being developed which are capable of taking fluorescent photographs by infra-red light in addition to color photographs by visible light and fluorescent photographs by visible light.

To use such an infra-red fundus camera, the fluorescent agent indocyanin green is first injected into a vein of the subject. Indocyanin green has the property of combining with protein in the subject's blood. Under illumination by infra-red light, the indocyanin green combined with protein fluoresces. A photograph of the fundus can thus be obtained using this fluorescence excited by the infra-red illumination.

In this fluorescent photography by infra-red illumination, the exposure conditions of the subject's eye vary with the time elapsed after the injection. The operator must therefore manually adjust the amount of light emitted from the photographic light source depending on this variation, and it is not possible to automatically set the amount of light from the illuminating source beforehand as can be done with color photography by visible light or fluorescent photography by visible light.

There are also individual differences in the protein concentrations of subjects which lead to fluctuations in the amount of indocyanin green combined with protein. Due to the large number of unknown factors, therefore, it is difficult to set the amount of light emitted by the illuminating light source automatically.

One way of overcoming this problem would be to provide this type of fundus camera with a selector switch in the manufacturing stage which selects between automatic setting and manual setting of the amount of light emitted by the photographic light source.

If such an automatic/manual selector switch were provided, however, there is a risk that the operator might forget to operate it.

For example, the switch might be left in the automatic position when a good photograph could have been obtained in the fluorescent mode using infra-red light only with a manual setting. Conversely, the switch might be left in the manual position when a good photograph could have been obtained with an automatic setting in a mode other than the fluorescent mode using infra-red light (i.e. color photography with visible light, or fluorescent photography with visible light).

Alternatively, the camera could be set manually for all photographic modes. If automatic setting of the amount of light gives good photographs in the color mode using visible light and fluorescent mode using visible light, however, there is no need to go to the trouble of adjusting the camera manually, and although a selector switch would then be rendered unnecessary, the operation of the camera would be unnecessarily complicated.

The problem of adjusting the amount of light when taking photographs could not therefore be conveniently resolved whatever arrangement was adopted.

SUMMARY OF THE INVENTION

It is therefore an object of this invention to provide a fundus camera which can take fluorescent photographs by infra-red light or other types of photographs, wherein good photographs are obtained without any special care as to the setting of the amount of light emitted by the source.

To achieve this object, the invention provides a fundus camera which can take fluorescent photographs by infra-red light or other types of photographs characterized in that it comprises detecting means for detecting whether or not the photograph being taken is a fluorescent photograph by infra-red light, means for automatically setting the amount of light emitted by the photographic source when the photograph being taken is not a fluorescent photograph by infra-red light, and changing over to manual setting of the amount of light emitted by the photographic source when the photograph being taken is a fluorescent photograph by infra-red light, according to information provided by the detecting means.

The fundus camera of this invention therefore detects whether the photograph being taken is a fluorescent photograph by infra-red light or another type of photograph. The change-over means functions as a means for automatically setting the amount of light emitted by the photographic light source when the photograph being taken is not a fluorescent photograph by infra-red light as determined by the detecting means, and changing over to a manual setting of the amount of light emitted by the photographic light source when the photograph being taken is a fluorescent photograph by infra-red light.

BRIEF DESCRIPTION OF THE DRAWINGS

FIG. 1 shows the whole arrangement of one embodiment of the fundus camera of this invention.

DESCRIPTION OF THE PREFERRED EMBODIMENTS

In FIG. 1, 1 is an illuminating optical system and 2 is a photographic optical system. The illuminating optical system 1 broadly comprises a halogen lamp 3 as an observation light source, a condensing lens 4, a xenon lamp 5 as a photographic light source, a condensing lens 6, a ring-shaped diaphragm 7, a relay lens 8, a mirror 9 and a relay lens 10.

The photographic optical system 2 comprises an objective lens 11, a perforated mirror 12, a focusing lens 13, an image-forming lens 14, a selecting mirror 15, a quick return mirror 16 and a film 17. The objective lens 11 faces the subject's eye 18. The ring-shaped diaphragm 7 and the pupil 19 of the subject's eye 18 are arranged in substantially conjugate positions with respect to the relay lenses 8, 10 and the objective lens 11.

When making observations, illuminating light from the halogen lamp 3 is led into the subject's eye 18 through the condensing lenses 4, 6, ring-shaped diaphragm 7, relay lens 8, mirror 9, relay lens 10, perforated mirror 12 and objective lens 11 so as to illuminate the fundus 20 of the subject's eye 18. When this illuminating light passes through the pupil 19 of the subject's eye 18, it becomes ring-shaped. When taking photographs, the xenon lamp 5 is switched on by operating a switch, not shown.

The light beam from the fundus 20 is led to the perforated mirror 12 through the objective lens 11, and passes through the perforation 12a of the perforated mirror 12, focusing lens 13 and image-forming lens 14 to reach the selecting mirror 15. For film recordings, the selecting mirror 15 is moved out of the optical path of the photographic optical system 2. For image display purposes, on the other hand, the selecting mirror 15 is inserted in the optical path of the photographic optical system 2. The selecting mirror 2 forms part of a television image-receiving system 21 which comprises a mirror 30, a relay lens 31 and a TV camera 32. The TV camera 32 converts the optical image to an electrical signal which is input to a processing circuit 35. The processing circuit 35 then outputs an image signal (composite signal) to a television monitor 36 based on the converted signal from the camera. The television monitor displays an image of the fundus, for example.

The quick return mirror 16 is inserted in the optical path of the photographic optical system 2 when taking photographs by visible light. The light beam from the fundus 20 is then reflected by this quick return mirror 16, and the reflected beam enters the operator's eye 25 through a mirror 23 and a lens 24 of the eyepiece system 22. The fundus 20 of the subject's eye 18 may then be observed. When taking color photographs by visible light or fluorescent photographs by visible light, the xenon lamp 5 is switched on by a switch not shown. The fundus 20 is illuminated by the light from the xenon lamp 5, and the quick return mirror 16 is moved out of the optical path of the photographic optical system 2. The light beam from the fundus 20 is then led to the film 17 where film recording takes place. Further, when taking fluorescent photographs by visible light, the fluorescent agent fluorescein is injected into a vein of the subject. When the fundus 20 is illuminated by visible light, the fluorescein is excited to fluoresce.

Exciter filters 26, 27 can be inserted in the optical path of the illuminating system 1 between the mirror 9 and the relay lens 8. The exciter filter 26 is inserted in the optical path of the illuminating system 1 when taking fluorescent photographs by visible light. The exciter filter 27 is inserted in the optical path of the illuminating system 1 when taking fluorescent photographs by infrared light (wavelength 800 nm-950 nm). Barrier filters 28, 29 can also be inserted between the perforated mirror 12 and the focusing lens 13 of the photographic optical system 2. The barrier filter 28 is inserted in the optical path of the photographic optical system 2 when taking fluorescent photographs by visible light. The barrier filter 29 is inserted in the optical path of the photographic optical system 2 when taking fluorescent photographs by infra-red light. Further, when taking color photographs (or black-and-white photographs) by visible light, the exciter filters 26, 27 are both moved out of the optical path of the illuminating system 1. Similarly, the barrier filters 28, 29 are moved out of the optical path of the photographic optical system 2.

A detecting switch 40a is arranged adjacent to the exciter filter 26. This detecting switch 40a detects whether or not the exciter filter 26 is inserted in the optical path. The detecting switch 40a emits an [H] signal when the exciter filter 26 is not in the optical path, and an [L] signal when it is in the optical path. Similarly, a detecting switch 40b is arranged adjacent to the exciter filter 27. This detecting switch 40b detects whether or not the exciter filter 27 is inserted in the optical path. The detecting switch 40b emits an [H] signal when the exciter filter 27 is not in the optical path, and an [L] signal when it is in the optical path.

The detecting switch 40a is connected to one terminal 41a of an AND circuit 41, to one terminal 42a of an AND circuit 42 via an inverter 44, and to one terminal 43a of an AND circuit 43. Further, the detecting switch 40b is connected to another terminal 41b of the AND circuit 41, to another terminal 42b of the AND circuit 42, and to another terminal 43b of the AND circuit 43 via an inverter 45. The output of the AND circuit 41 is input to an automatic light setting mode circuit 50. The output of the AND circuit 42 is input to an automatic light setting mode circuit 51. The output of the AND circuit 43 is input to a manual light setting mode circuit 52. The automatic light setting mode circuit 50 automatically sets the amount of light emitted by the xenon lamp 5 based on exposure conditions such as the sensitivity of the film 17 and shutter speed, etc., when taking color photographs (or black-and-white photographs) by visible light. Similarly, the automatic light setting mode circuit 51 automatically sets the amount of light emitted by the xenon lamp 5 based on exposure conditions such as the sensitivity of the film 17 and shutter speed, etc., when taking fluorescent photographs by visible light. The change-over circuit 46 comprises the AND circuits 41, 42, 43, the inverter circuits 44, 45, the automatic light setting mode circuits 50, 51 and the manual setting circuit 52.

The reason why the automatic light setting mode was chosen for taking fluorescent photographs by visible light is that there is expected to be some degree of correspondence between the amount of fluorescence emitted by fluorescein and the amount of illumination provided by visible light.

When taking color photographs by visible light, [H] signals are input to the AND circuit 41 from the detector switch 40a and the detector switch 40b without modification. The AND circuit 41 then outputs an [H] signal to the automatic light setting mode circuit 50, and the automatic light setting mode circuit 50 automatically sets the amount of light emitted by the xenon lamp circuit 47. As the [H] signal from the detecting switch 40a is inverted before being input to the AND circuit 42, and the [H] signal from the detecting switch 40b is inverted before being input to the AND circuit 43, the automatic light setting mode circuit 51 and the manual light setting circuit 52 do not operate.

When taking fluorescent photographs by visible light, an [L] signal from the detecting switch 40a and an [H] signal from the detecting switch 40b are input to the AND circuit 41, so the output of the AND circuit 41 is [L]. The [L] signal from the detecting switch 40a is however inverted by the inverter 44 before being input to the AND circuit 42. [H] signals are therefore input to both terminals of the AND circuit 42, and the output of the AND circuit 42 is [H]. The automatic light setting mode circuit 51 therefore operates, and automatically sets the amount of light emitted by the xenon lamp circuit 47.

When taking fluorescent photographs by infra-red light, an [H] signal from the detector switch 40a and a [L] signal from the detector switch 40b are input to the AND circuit 41, so the output of the AND circuit 41 is also [L]. The [H] signal from the detector switch 40a is inverted before being input to the AND circuit 42, and a [L] signal is also input from the detector switch 40b. [L] signals are therefore input to both terminals of the AND circuit 42, and the output of the AND circuit 42 is [L]. The automatic light setting mode circuit 51 therefore does not operate.

The [L] signal from the detector switch 40b is inverted by the inverter 45 before being input to the AND circuit 43, while at the same time an [H] signal is input from the detector switch 40a. [H] signals are therefore input to both terminals of the AND circuit 43, the output of the AND circuit 43 is [H], and the manual light setting mode circuit 52 becomes functional. The manual light setting mode circuit 52 then allows manual setting of the xenon lamp circuit 47.

When the change-over circuit 46 has made it possible to perform manual setting of the xenon lamp circuit 47, the amount of light emitted by the xenon lamp 5 may be manually adjusted by operating a control 48a of a xenon lamp emission regulator 48.

In the present embodiment, the construction is such that assessment of whether or not the photograph being taken is a fluorescent photograph by infra-red light is made by detecting whether or not the exciter filters are inserted in the optical path of the illuminating system 1. The construction may however also be such that this assessment is made by detecting whether or not the barrier filters are inserted in the optical path of the photographic optical system 2. And may also be such that this assessment is made to manual setting of the amount of light emitted by the photographic light source only be detecting whether or not the filters used when the photograph is taken by infra-red light are inserted in the optical path.

The construction may also be such that a change-over is made to manual setting of the amount of light emitted by the xenon lamp 5 by pressing a button to set fluorescent photography by infra-red light, and a change-over is made to automatic setting of the amount of light emitted by the xenon lamp 5 by pressing a button to set photography by a mode different from fluorescent photography by infra-red light.

Further, the construction may also be such that a change-over is made to automatic setting of the amount of light emitted by the photographic light source when the photograph being taken is a colored photograph by visible light, and to manual setting of the amount of light emitted by the photographic light source when the photograph being taken is a fluorescent photograph by visible light and by infra-red light.

What is claimed is:

1. A fundus camera which can take fluorescent photographs by infra-red light and other types of photographs, characterized in that it comprises:
   detecting means for detecting whether or not the photograph being taken is a fluorescent photograph by infra-red light,
   means for automatically setting the amount of light emitted by a photographic source when the photograph being taken is not a fluorescent photograph by infra-red light, and changing over to manual setting of the amount of light emitted by said photographic source when the photograph being taken is a fluorescent photograph by infra-red light, according to information provided by said detecting means.

2. A fundus camera which can take fluorescent photographs by infra-red light and color photographs by visible light, characterized in that it comprises:
   detecting means for detecting whether or not the photograph being taken is a fluorescent photograph by infra-red light,
   means for automatically setting the amount of light emitted by a photographic source when the photograph being taken is a color photograph by visible light, and changing over to manual setting of the amount of light emitted by said photographic source when the photograph being taken is a fluorescent photograph by infra-red light, according to information provided by said detecting means.

3. A fundus camera as defined in claim 1 characterized in that said detecting means consists of a detecting switch arranged adjacent to and such it can engage with an exciter filter that is inserted in the optical path of an illuminating system when infra-red illumination is being used.

4. A fundus camera as defined in claim 1 characterized in that said detecting means consists of a detecting switch arranged adjacent to and such that it can engage with a barrier filter that is inserted in the optical path of a photographic system when infra-red illumination is being used.

5. A fundus camera which can take fluorescent photographs by infra-red light and fluorescent photographs by visible light, characterized in that it comprises:
   detecting means for detecting whether or not the photograph being taken is a fluorescent photograph by infra-red light,
   means for automatically setting the amount of light emitted by a photographic source when the photograph being taken is a fluorescent photograph by visible light, and changing over to manual setting of the amount of light emitted by said photographic source when the photograph being taken is a fluorescent photograph by infra-red light, according to information provided by said detecting means.

6. A fundus camera which can take fluorescent photographs by infra-red light and other types of photographs, characterized in that it comprises:
   means for automatically setting the amount of light emitted by a photographic source when the photograph being taken is not a fluoroscent photograph by infra-red light, and changing over to manual setting of the amount of light emitted by said photographic source when the photograph being taken is a fluorescent photograph by infra-red light depending on the operation to set the photographic mode, 7. A fundus camera which can take fluorescent photographs by infra-red light and other types of photographs, characterized in that it comprises:
   means for automatically setting the amount of light emitted by a photographic source when the photograph being taken is a colored photograph, and changing over to manual setting of the amount of light emitted by said photographic source when the photograph being taken is a fluorescent photograph by infra-red light and visible light depending on the operation to set the photographic mode.

* * * * *

UNITED STATES PATENT AND TRADEMARK OFFICE
CERTIFICATE OF CORRECTION

PATENT NO. : 5,181,055
DATED : January 19, 1993
INVENTOR(S) : Eiichi Sano, et al.

It is certified that error appears in the above-identified patent and that said Letters Patent is hereby corrected as shown below:

Claim 3, Column 6, Line 21 before "it" insert --that--.

Signed and Sealed this

First Day of February, 1994

Attest:

BRUCE LEHMAN

Attesting Officer

Commissioner of Patents and Trademarks